(12) United States Patent
Chang et al.

(10) Patent No.: US 6,365,767 B1
(45) Date of Patent: Apr. 2, 2002

(54) PROCESS FOR CO-PRODUCTION OF DIALKYL CARBONATE AND ALKANEDIOL

(75) Inventors: Clarence D. Chang, Princeton; Zhaozhong Jiang, Thorofare; Rene B. LaPierre, Medford, all of NJ (US); Suzanne E. Schramm, Glen Mills, PA (US); Hye Kyung Cho Timken, Woodbury, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/322,880

(22) Filed: Aug. 20, 1999

(51) Int. Cl.[7] ............................................... C07C 69/96
(52) U.S. Cl. ........................................................ 558/277
(58) Field of Search .......................................... 558/277

(56) References Cited

U.S. PATENT DOCUMENTS

| | | |
|---|---|---|
| 3,642,858 A | 2/1972 | Frevel et al. |
| 4,062,884 A | 12/1977 | Romano et al. |
| 4,181,676 A | 1/1980 | Buysch et al. |
| 4,391,739 A | 7/1983 | Chu |
| 4,434,105 A | 2/1984 | Buysch et al. |
| 4,661,609 A | 4/1987 | Knifton |
| 4,686,274 A | 8/1987 | Harris et al. |
| 4,691,041 A | 9/1987 | Duranleau et al. |
| 4,895,970 A | 1/1990 | Harris |
| 5,015,753 A | 5/1991 | Harris |
| 5,218,135 A | 6/1993 | Buysch et al. |
| 5,231,212 A | 7/1993 | Buysch et al. |
| 5,292,980 A | 3/1994 | Dessau |
| 5,430,170 A | 7/1995 | Urano et al. |
| 5,436,362 A | 7/1995 | Kondoh et al. |
| 5,489,703 A | 2/1996 | Pacheco et al. |
| 5,498,743 A | 3/1996 | Shih et al. |
| 5,663,480 A | 9/1997 | Tsuneki et al. |

FOREIGN PATENT DOCUMENTS

| | | |
|---|---|---|
| EP | 0 478 073 A2 | 9/1991 |
| JP | 3[1001]-44354 | 2/1991 |

OTHER PUBLICATIONS

Knifton, J.F. and Duranleau, R.G., "Ethylene Glycol–Dimethyl Carbonate Cogeneration," *J. of Molecular Catalysis* 67:389–399(1991).

Watanabe, Y. and Tatsumi T., "Hydrotalcite–type Materials as Catalysts for the Synthesis of Dimethyl Carbonate from Ethylene Carbonate and Methanol[1]," *Microporous and Mesoporous Materials* 22:399–407(1998).

Chang, C.D., *Handbook of Heterogenous Catalysis*, Wiley–VCH:Weinheim, Germany, vol. 4, Chapter 3.7 (1997).

Yagi, F., Kanuka, N., Tsuji, H., Nakata, S., Kita, H. and Hattori, H., "[133]Cs and $^{23}$Na MAS NMR studies of zeolite X containing cesium," *Microporous Materials* 9:229–235(1997).

Skibsted, J., Vosegaard, T., Bildsøe, H. and Jakobsen, H.J., "[133]Cs chemical Shielding Anisotropics and Quadrupole Couplings from Magic–Angle Spinning NMR of Cesium Salts," *J. Phys. Chem.*, 100:14872–14881(1996).

*Primary Examiner*—Joseph K. McKane
*Assistant Examiner*—Joseph Murray

(57) ABSTRACT

A method is provided for co-producing dialkyl carbonate and alkanediol by reacting alkylene carbonate with alkanol in the presence of a zeolite catalyst which contains alkali metal, alkaline earth metal, or a combination thereof present in excess of a stoichiometric amount.

10 Claims, 4 Drawing Sheets

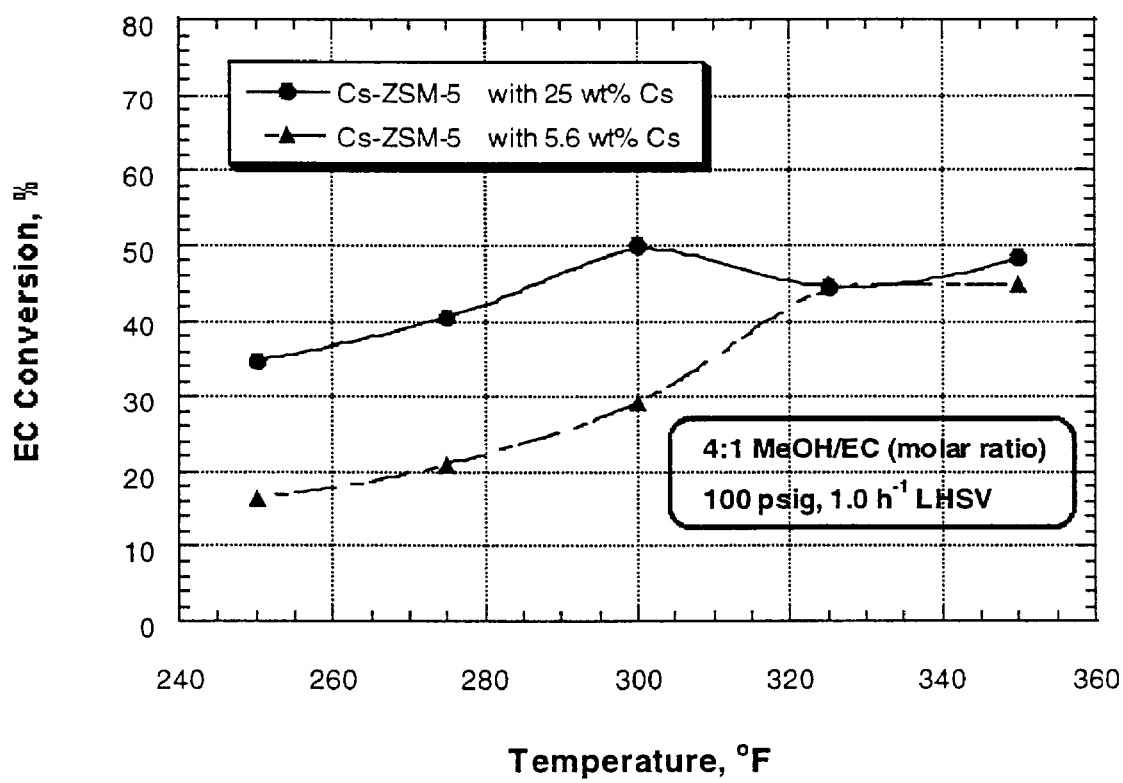
Figure 1. Comparison of EC Conversion vs Temperature between Stoichiometric Cs-ZSM-5 and Cs-ZSM-5 Containing Cesium in Excess of a Stoichiometric Amount

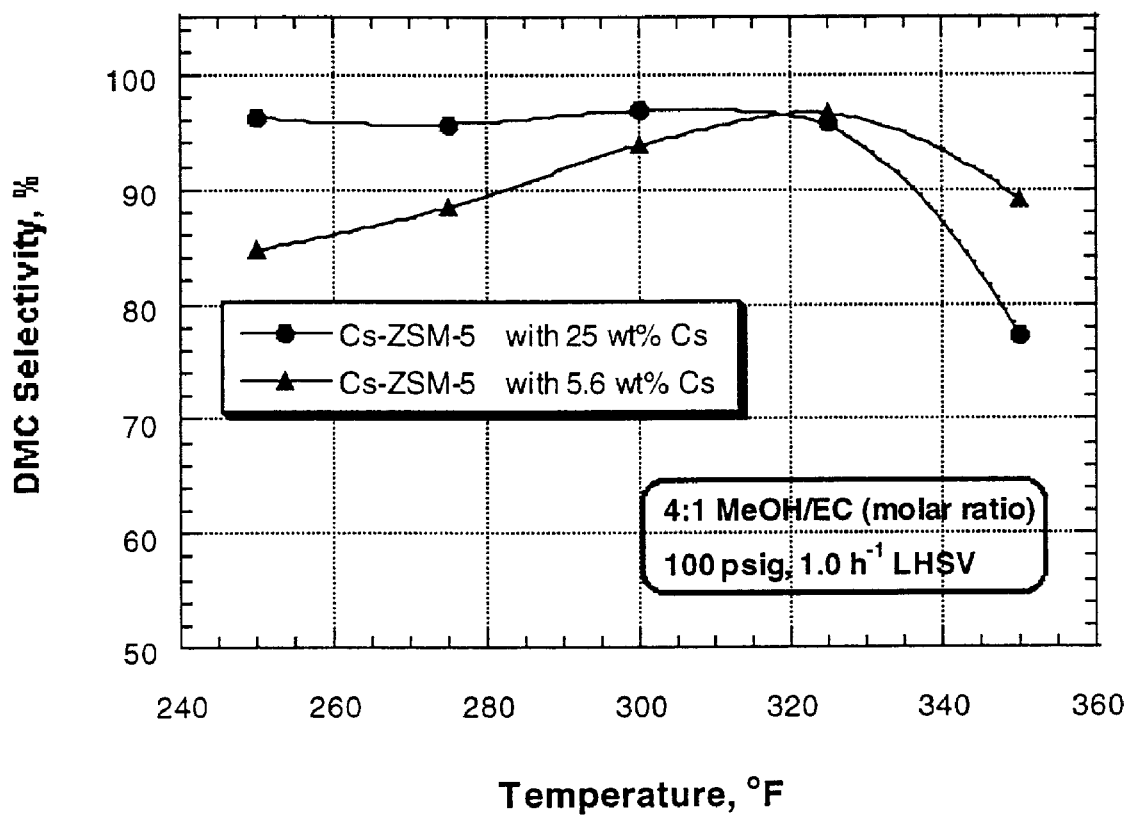
Figure 2. Comparison of DMC Selectivity vs Temperature between Stoichiometric Cs-ZSM-5 and Cs-ZSM-5 Containing Cesium in Excess of a Stoichiometric Amount

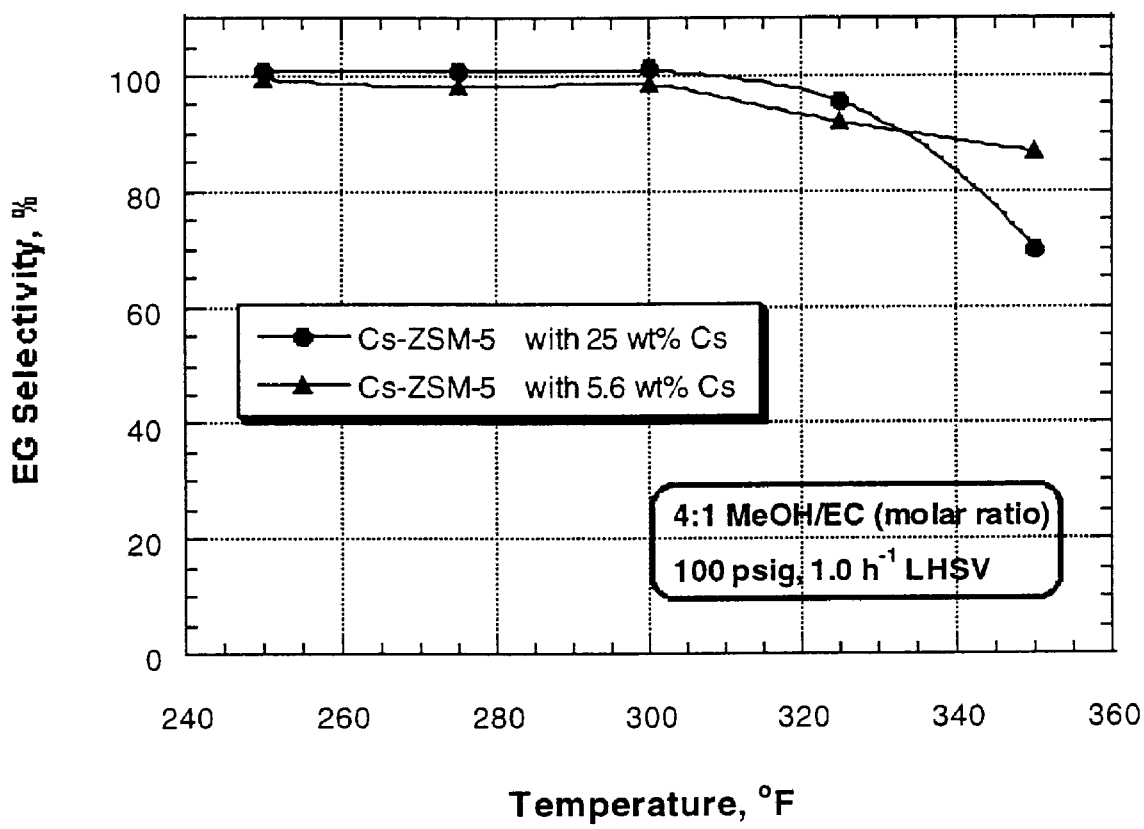
Figure 3. Comparison of EG Selectivity vs. Temperature between Stoichiometric Cs-ZSM-5 and Cs-ZSM-5 Containing Cesium in Excess of a Stoichiometric Amount

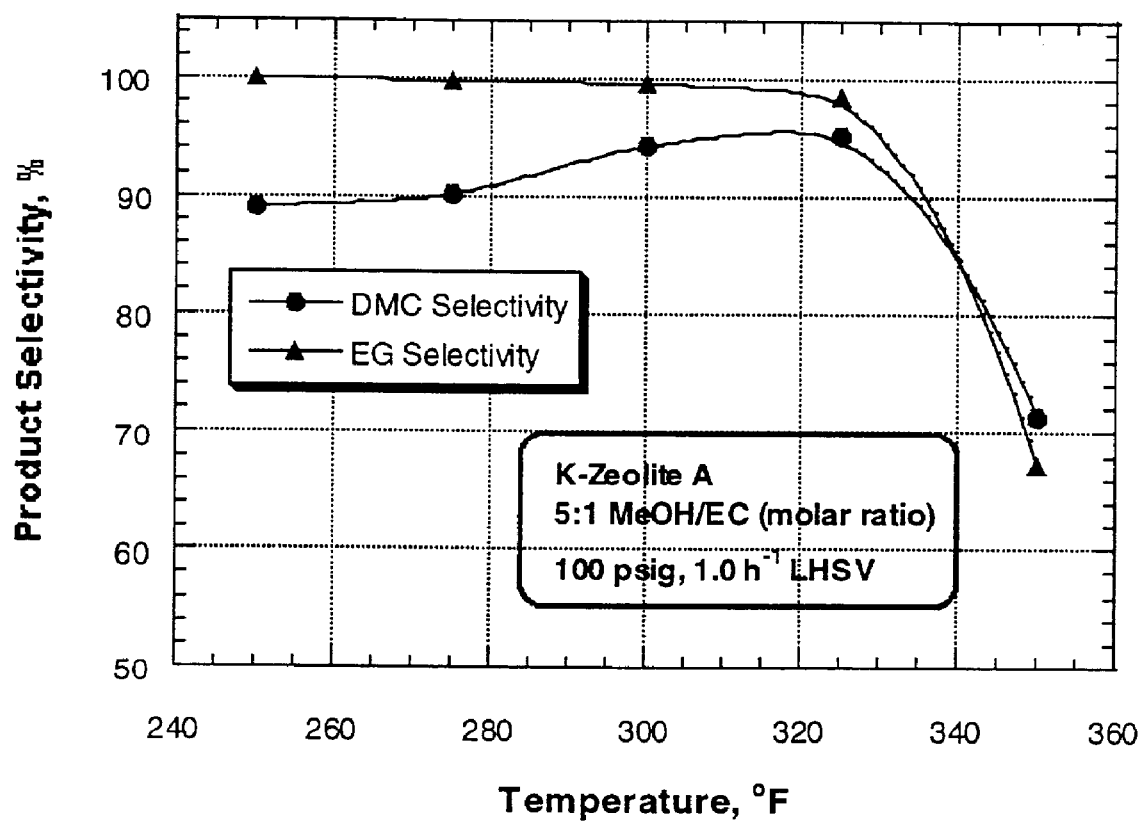
Figure 4. DMC and EG Selectivity vs Temperature for the MeOH/EC Reaction Catalyzed by K-zeolite A

PROCESS FOR CO-PRODUCTION OF DIALKYL CARBONATE AND ALKANEDIOL

BACKGROUND

This invention relates to a method of co-producing dialkyl carbonate and alkanediol, and, in particular, to a method for enhancing the efficiency of the co-production by the use of zeolite supported alkali and/or alkaline earth metal present in excess of a stoichiometric amount.

Various homogeneous catalysts have been proposed for carbonate transesterification. For example, U.S. Pat. Nos. 3,642,858 and 4,181,676 disclose the preparation of dialkyl carbonates by tranesterifying alkylene carbonates with alcohols in the presence of alkali metals or alkali metal compounds without the use of a support material. U.S. Pat. No. 4,661,609 teaches the use of a catalyst selected from the group consisting of zirconium, titanium and tin oxides, salts or complexes thereof.

Commercial use of homogeneous catalysts is restricted because separation of the catalyst from the reactants can be difficult. Because the transesterification is an equilibrium reaction, in an attempt to isolate the intended dialkyl carbonate by distillation of the reaction liquid without advance separation of the catalyst, the equilibrium is broken during the distillation and a reverse reaction is induced. Thus, the dialkyl carbonate once formed reverts to alkylene carbonate. Furthermore, due to the presence of the homogenous catalyst, side reactions such as decomposition, polymerization, or the like concurrently take place during the distillation which decrease the efficiency.

Various heterogenous catalysts have also been proposed for carbonate transesterification. The use of alkaline earth metal halides is disclosed in U.S. Pat. No. 5,498,743. Knifton, et al., "Ethylene Glycol-Dimethyl Carbonate Cogeneration," *J. Molec. Catal.* 67:389–399 (1991) disclose the use of free organic phosphines or organic phosphines supported on partially cross-linked polystyrene. U.S. Pat. No. 4,691,041 discloses the use of organic ion exchange resins, alkali and alkaline earth silicates impregnated into silica, and certain ammonium exchanged zeolites. U.S. Pat. No. 5,430,170 discloses the use of a catalyst containing a rare earth metal oxide as the catalytically active component. The use of hydrotalcites is disclosed in Japanese patent application 3[1991]-44,354. Zeolites ion-exchanged with alkali metal and/or alkaline earth metal, thereby containing a stoichiometric amount of metal, are disclosed in U.S. Pat. No. 5,436,362.

Inorganic heterogenous catalysts generally possess thermal stability and easy regeneration. However, these catalysts, including the zeolites containing a stoichiometric amount of alkali or alkaline earth metal, generally demonstrate low activity and/or selectivity and are unsatisfactory for commercial application.

Polymer supported organic phosphines and ion exchange resins show high activity and good to excellent selectivity in transesterification reaction between alkylene carbonate and alkanol; however, these polymeric materials do not appear very stable and gradually lose catalytic activity over a long period of time, especially at relatively high temperatures.

Thus, there remains a need for a method of transesterifying alkylene carbonate with alkanol to co-produce dialkyl carbonate and alkanediol which will provide higher activity and selectivity over a wide temperature range.

SUMMARY OF INVENTION

A method is provided for co-producing dialkyl carbonate and alkanediol by reacting alkylene carbonate with alkanol in the presence of a zeolite catalyst which contains alkali metal, alkaline earth metal, or a combination thereof present in excess of a stoichiometric amount.

The preferred alkylene carbonate is ethylene carbonate and the preferred alkanol is methanol. Cesium is the preferred alkali metal.

The zeolite can be selected from the group consisting of ZSM-5, zeolite beta, ZSM-22, ZSM-23, ZSM-48, ZSM-35, ZSM-11, ZSM-12, Mordenite, Faujasite, Erionite, zeolite USY, MCM-22, MCM-49, MCM-56, and SAPO; ZSM-5 is most preferred.

Alkali metal, alkaline earth metal, or combination thereof can be incorporated into the zeolite by any known means which will allow at least a portion of the excess metal to occupy the zeolite pore space; such as by impregnation. In a preferred embodiment, alkali metal and/or alkaline earth metal within the zeolite pore is in an oxide form. For example, when cesium is used as the alkali metal, the excess cesium occupies the zeolite pore in the form of cesium oxide.

The process conditions include a reaction temperature of about 20° C. (68° F.) to about 300° C. (572° F.), a reaction pressure of about 14 to about 4000 psig, a liquid hour space velocity of about 0.1 to 40 hr$^{-1}$, and a molar ratio of alkanol to alkylene carbonate of about 1–20.

The transesterification catalysts of the current invention exhibit high activity and excellent selectivity in the reaction of alkylene carbonate with alkanol and are superior vs. zeolites in $NH_4^+$-form or containing stoichiometric amount of alkali and/or alkaline earth metal.

Unlike polymer catalysts such as ion exchange resins, the basic zeolite catalysts used in the method of the invention are thermally stable and regenerable. The combination of high catalytic activity and selectivity in a wide temperature range, and excellent thermal stability and regenerability of the catalyst render them suitable for commercial use in co-producing organic carbonate and alkanediol through ester exchange reaction.

The organic carbonates produced by the method of the invention, dimethyl carbonate in particular, have potential application as "green" replacements for phosgene that is used mainly in manufacture of polyurethane and polycarbonate resins.

BRIEF DESCRIPTION OF DRAWINGS

FIG. 1 is a graph demonstrating EC (ethylene carbonate) conversion vs. temperature for the MeOH/EC reaction between a stoichiometric Cs-ZSM-5 catalyst and a method of the invention using a Cs-ZSM-5 catalyst containing cesium in excess of a stoichiometric amount.

FIG. 2 is a graph demonstrating DMC (dimethyl carbonate) selectivity vs. temperature for the MeOH/EC reaction between a stoichiometric Cs-ZSM-5 catalyst and a method of the invention using a Cs-ZSM-5 catalyst containing cesium in excess of a stoichiometric amount.

FIG. 3 is a graph demonstrating EG (ethylene glycol) selectivity vs. temperature for the MeOH/EC reaction between a stoichiometric Cs-ZSM-5 catalyst and a method of the invention using a Cs-ZSM-5 catalyst containing cesium in excess of a stoichiometric amount.

FIG. 4 is a graph demonstrating DMC and EG selectivity vs. temperature for the MeOH/EC reaction catalyzed by K-zeolite A.

DETAILED DESCRIPTION OF INVENTION

In accordance with the present invention, a method is provided for the catalyzed co-production of dialkyl carbonate and alkanediol through the transesterification of an alkylene carbonate with alkanol. The catalyst is a zeolite containing alkali metal, alkaline earth metal, or combination thereof in excess of a stoichiometric amount.

Generally, all alkylene carbonates can be used as a reactant in this invention. However, lower alkylene carbonate such as ethylene carbonate, propylene carbonate, butylene carbonate or the like is preferred; ethylene carbonate or propylene carbonate is most preferred.

Generally, all alkanol reactants can be used, provided the alkanol reacts with cyclocarbonate to produce the dialkyl carbonate and alkanediol product. However, an aliphatic or aromatic alkanol having 1 to 10 carbon atoms is preferably used. For example, methanol, ethanol, n-propanol, iso-propanol, n-butanol, iso-butanol, secondary butanol, tertiary butanol, allyl alcohol, pentanol, cyclo-hexanol, benzyl alcohol, 2-phenyl ethyl alcohol, 3-phenyl propyl alcohol, 2-methoxy ethanol or the like can be used as the aliphatic or aromatic alcohol. A lower aliphatic alcohol such as methanol is most preferably used due to its reactivity and low cost.

Further, a phenolic compound can be used in place of the alcoholic compound as the compound which has a hydroxyl (OH) group and reacts with cyclocarbonate to produce the carbonate.

The support for the catalyst used in the method of the invention is a zeolite. It should be noted, however, that the zeolite acts as more than simply a support. Rather, the unique crystalline pore structure of the zeolite is important in retaining excess alkali and/or alkaline earth metal. Examples of zeolites which are suitable supports for the catalyst used in the method of the invention include ZSM-5, zeolite beta, ZSM-22, ZSM-23, ZSM-48, ZSM-35, ZSM-11, ZSM-12, Mordenite, Faujasite, Erionite, zeolite USY, MCM-22, MCM-49, MCM-56, and SAPO. ZSM-5, zeolite beta, and MCM-22 are preferred; ZSM-5 is most preferred.

The catalyst contains alkali metal (Li, Na, K, Rb, Cs), alkaline earth metal (Be, Mg, Ca, Sr, Ba), or combination thereof belonging to IA group and/or IIA group in the periodic table of elements. Alkali metal and alkaline earth metal are both defined to include compounds containing these metals. Cesium is the preferred metal.

The catalyst utilized in the method of the invention contains alkali and/or alkaline earth metal in excess of a stoichiometric amount. By "excess of a stoichiometric amount", it is meant that the molar ratio of alkali metal to structural aluminum in the zeolite support is greater than 1 or that the molar ratio of alkaline earth metal to structural aluminum is greater than 0.5. If a combination of alkali metal and alkali earth metal is used, "excess of a stoichiometric amount" can be represented by the equation:

[(moles of alkali metal)+2(moles of alkali earth metal)]/(moles of zeolite Al)>1      (1)

If the zeolite support is SAPO, the presence of alkali and/or alkaline earth metal in excess of a stoichiometric amount means that the metal content is greater than the maximum amount of metal which is exchangeable with the SAPO support.

There is no upper limit to the amount of excess alkali and/or alkaline earth metal. However, the excess alkali and/or alkaline earth metal which is reactive preferably resides within the pore of the zeolite. If additional alkali or alkaline earth metal is added, it will reside outside the pore area and will most likely be flushed away by the reagents. Besides wasting the metal catalyst, this may cause an initial decrease in activity along with problems typically associated with homogeneous catalysts.

Alkali and/or alkaline earth metal may be incorporated into the zeolite support by any known means, such as impregnation or ion exchange/impregnation combination; which will allow the metal cations to neutralize the acid sites within the zeolite as well as allow at least a portion of alkali and/or alkaline earth metal to occupy the zeolite pore space. Alkali and/or alkaline earth metal occupying the zeolite pore space can be part of a compound containing the metal. It is preferred that alkali and/or alkaline earth metal occupying the zeolite pore space be in oxide form.

Ion exchange alone is not a preferred method because the metal cations will occupy the ion exchange sites within the zeolite, but this method will not permit excess alkali and/or alkaline earth metal to reside within the pore space.

For example, a zeolite catalyst can be synthesized through ion-exchange with a metal sulfate in aqueous solution followed by removal of excess metal sulfate through washing with de-ionized water and calcining. The metal cations will then be predominantly associated with the polyanionic zeolite framework.

However, applicants have discovered that if a zeolite is synthesized through appropriate means using excess alkali and/or alkaline earth metal, some of the metal will remain in the zeolite pore and help drive the transesterification reaction to completion. For example, if a zeolite is prepared through impregnation using cesium sulfate in aqueous solution; upon drying and calcination, preferably at a temperature greater than 1000° F. (538° C.), the zeolite acid sites are neutralized by a cesium cation, while some of the cesium sulfate is decomposed to a cesium oxide which resides in the zeolite pore.

Without being bound by theory, the high activity of the method of the invention using a catalyst with excess alkali or alkaline earth metal is due to its content of strong base sites, e.g. alkali and/or alkaline earth metal oxides.

The high selectivity is attributable to the high alkali and/or alkaline earth metal content of the catalyst which inhibits its reaction with methanol to form Bronsted acid sites, thus suppressing acid catalyzed side reactions such as dehydration of alkanol and subsequent hydrolysis/decomposition of organic carbonate product.

To illustrate, during the reaction of ethylene carbonate (EC) with methanol (MeOH), especially at high temperatures, equilibrium methanolysis can occur as shown in following equation with "Metal" being alkali and/or alkaline earth metal:

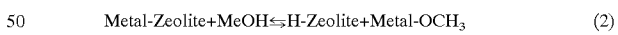

Metal-Zeolite+MeOH⇌H-Zeolite+Metal-OCH$_3$      (2)

Applicants have found that zeolites exchanged with a stoichiometric amount of alkali or alkaline earth metal gradually lose the metal when continuously treated with pure methanol at 60° C. (140° F.) under 50 psig pressure. It is anticipated that the resultant acid sites would catalyze and initiate dehydration of methanol to form dimethyl ether and water. Dimethyl ether can be further converted to hydrocarbons and water via MTG (Methanol To Gasoline) type reactions (See, Chang, C. D., *Handbook of Heterogenous Catalysis*, Wiley-VCH:Weinheim, Germany, Vol. 4, Chapter 3.7 (1997)). The resultant water can cause hydrolysis/decomposition of DMC/EC to generate carbon dioxide and corresponding alcohols. Dimethyl ether, $C_2$–$C_7$ hydrocarbons, and $CO_2$ have all been observed as byproducts during the EC/MeOH reaction. The following equations further illustrate the side reactions which can occur:

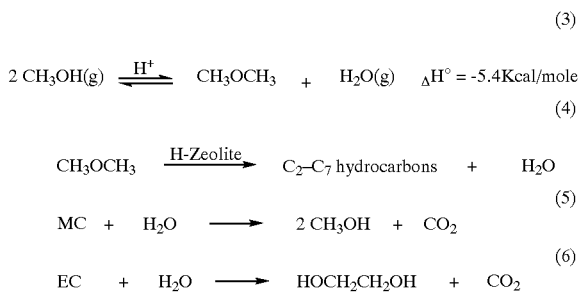

(3)

(4)

(5)

(6)

Since the methanolysis reaction is an equilibrium reaction, high alkali and/or alkaline earth metal content inhibits the formation of acid sites and maintains the catalyst in its base form. As a result, the side reactions discussed above are minimized and the catalyst selectivity is improved.

The acid initiated side reactions are more significant at lower temperatures due to the fact that gas phase dehydration of methanol to dimethyl ether is an exothermic equilibrium reaction and is more favorable at lower temperatures. In addition, lower feed conversion and higher methanol concentration at lower temperatures can further promote methanol dehydration. This explains why DMC selectivity decreases with decreasing temperature for EC/MeOH transesterification catalyzed by stoichiometric catalysts. The method of the invention using a catalyst containing excess alkali and/or alkaline earth metal, on the other hand, retains its selectivity with decreasing temperature.

The reactor type in this invention can be any type generally known such as a continuous fluid bed, fixed bed or stirred tank, etc. With the heterogenous catalyst used in the method of the invention, it is preferred that a fixed bed be used so as to avoid the expense of having to recover the catalyst from the reagents.

The reaction conditions of this invention include a reaction temperature of about 20° C. to about 300° C., preferably about 60° C. to about 175° C.; a reaction pressure of about 14 to about 4000 psig, preferably about 50 to about 400 psig; a liquid hour space velocity of about 0.1 to about 40 $hr^{-1}$, preferably about 0.5 to about 10 $hr^{-1}$; and a molar ratio of alkanol to alkylene carbonate of about 1 to 20, preferably about 2 to 8.

The following comparative examples are provided to assist in a further understanding of the invention. The particular materials and conditions employed are intended to be further illustrative of the invention and are not limiting upon the reasonable scope thereof.

EXAMPLE 1

This example describes a method for preparing three catalysts employed in the comparative examples. Cs-ZSM-5 with 25 wt % Cs is an example of a catalyst used in the method of the invention having alkali and/or alkaline earth metal in excess of a stoichiometric amount. Cs-ZSM-5 with 5.6 wt % Cs is an example of a stoichiometric catalyst. K-zeolite A (3A molecular sieves) is a commercially available catalyst, which also contains a stoichiometric amount of metal. The physical properties of the three zeolite samples are shown in Table 1.

TABLE 1

| Catalyst | BET Surface Area (m²/g) | Cs, wt % | S, wt % |
| --- | --- | --- | --- |
| Cs-ZSM-5 (excess Cs) | 225 | 25.1 | 1.64 |
| Cs-ZSM-5 (stoichiometric Cs) | 389 | 5.6 | 0.095 |
| K-zeolite A | 16 | — | — |

The Cs-ZSM-5 with 25 wt % Cs was prepared using 55:1 $SiO_2/Al_2O_3$ ratio ZSM-5. The ZSM-5 crystals were ammonium exchanged twice using 5 cc/ g of 1 M solution of $NH_4NO_3$ followed by drying at 250° F. (120° C.) overnight. The dried ZSM-5 was calcined under flowing $N_2$ at 900° F. (482° C.) for 3 hours. Air (2 v/v/min) was then gradually introduced and the temperature was raised to 1000° F. (538° C.) and maintained for 6 hours. The resulting H-form ZSM-5 crystals were impregnated with 25 wt % Cs using an aqueous solution of cesium sulfate via incipient wetness impregnation method. The Cs impregnated ZSM-5 was dried at 250° F. (121 ° C.) for overnight and calcined in air at 1000° F. (538° C.) for 3 hours. The powdery, crystalline catalyst was pelletized and sized to 60–80 mesh prior to catalyst evaluation.

The Cs-ZSM-5 with 5.6 wt % Cs was prepared also using H-form 55:1 $SiO_2/Al_2O_3$ ratio ZSM-5 (same as the one described above). The H-form ZSM-5 was exchanged two times using 0.5 M aqueous solution of $Cs_2SO_4$ (5 cc of Cs solution per gram of ZSM-5 was used). The Cs-exchanged ZSM-5 was then washed with deionized water 4 times, dried at 250° F. (120° C.) overnight, and calcined in air at 1000° F. (538° C.) for 3 hours. The powdery, crystalline catalyst was pelletized and sized to 60–80 mesh prior to catalyst evaluation.

K-zeolite A pellets (brand name: 3A molecular sieves) was obtained from Aldrich. The zeolite pellets was dried and sized to 60–80 mesh prior to catalyst evaluation.

EXAMPLE 2

This example describes the NMR characterization of the stoichiometric Cs-ZSM-5 (5.6 wt % Cs) and excess stoichiometric Cs-ZSM-5 (25 wt % Cs) catalysts.

500.13 MHZ $^1H$ MAS NMR spectra were obtained on a 500 MHZ Bruker AMX spectrometer using 10.0 kHz sample spinning, 7.0 μs 90 degree excitation pulses, and a 60 s recycle time. $H_2O$ was used as the external chemical shift reference. The samples were dried overnight at 400° C. (752° F.) under vacuum prior to packing the samples in a glove box and obtaining the $^1H$ NMR spectra. 65.6 MHZ $^{133}Cs$ MAS NMR spectra were obtained on a 500 MHZ Bruker AMX spectrometer using 10.0 kHz sample spinning, short 0.8 μs excitation pulses, and a 0.5 s recycle time. 0.5M CsCl was the external chemical shift and quantitation standard. All samples were equilibrated at 100% humidity prior to obtaining the $^{133}Cs$ NMR spectrum.

The $^{133}Cs$ NMR spectrum of Cs-ZSM-5 with 25 wt % Cs shows two resonance absorptions at 68 and 100 ppm due to unreacted, crystalline $Cs_2SO_4$ (See, Skibsted, J. et al., *J. Phys. Chem.*, 100:14872 (1986)), in addition to a broad absorbance at 22 ppm due to cesium cations, including those of cesium oxide, within the zeolite pore. The Cs chemical shift is dominated by the location of the Cs in the zeolite and not by the strength of the acid site where the Cs is exchanged. See, Yagi, F., et al., *Microporous Mater.*, 9:229

(1997). Cesium cations located on zeolite surface would have a lower chemical shift. Solid state $^1$H-NMR spectra of both catalysts (25 wt % Cs and 5.6 wt % Cs) indicate an absence of Bronsted acid protons at ~4.0 ppm; thus, complete cesium exchange was achieved in both cases. However, based on the results of elemental analysis, the impregnated catalyst containing excess cesium demonstrated 5.4 wt % Cs that is associated with zeolite framework, 6.1 wt % Cs in $Cs_2O$ form, and 13.6 wt % Cs as $Cs_2SO_4$; thereby evidencing cesium oxide in the zeolite pores.

EXAMPLE 3

Transesterification experiments were performed using each of the catalysts described in Example 1. The catalysts were utilized in the transesterification of ethylene carbonate (EC) with methanol (MeOH) to form dimethyl carbonate (DMC) and ethylene glycol (EG).

The experiments were run in a fixed bed microunit equipped with a three-zone furnace and a down-flow trickle-bed tubular reactor (½" ID). The catalysts were sized to 60–80 mesh, and the reactor was loaded with a mixture of 10 cc of the sized catalyst and 3 cc of 80–120 mesh sand.

After pressure testing of the unit, the catalyst was dried at 400° F. (204° C.) for two hours under 1 atmosphere, 170 cc/min nitrogen flow. At the end of this period, the reactor was cooled down to 150° F. (66° C.) and nitrogen flow was stopped. The reactor pressure, controlled by a pressure regulator, was then set to 100 psi, and the EC/methanol mixture feed was pumped and added to the top of the reactor at 1.0 h$^{-1}$ LHSV. The reactor temperature was gradually increased to initial operating temperature of 250° F. (121 ° C.). Each material balance was typically started after the reactor was conditioned for eight hours. Liquid products were condensed in a stainless steel dropout pot at −10° C. (~14° F.). Off-gas was measured in volume using a wet gas meter. Both liquid and off-gas products were analyzed by GC. The catalytic reaction was studied at various temperatures and LHSV to vary EC conversion.

The detailed operating conditions, feed ratio, material balance data, and results on EC conversion and dimethyl carbonate (DMC)/ethylene glycol (EG) selectivities for Cs-ZSM-5 containing 25 wt % cesium are summarized in Table 2.

TABLE 2

Transesterification of Ethylene Carbonate with Methanol Catalyzed by Cs-ZSM-5 with 25 wt % Cs (Condition: 100 psig)

| Temperature, ° F./° C. | 250/121 | 275/135 | 300/149 | 325/163 | 350/177 |
|---|---|---|---|---|---|
| WHSV, h$^{-1}$ | 1.3 | 1.3 | 1.3 | 1.3 | 1.3 |
| LHSV, h$^{-1}$ | 1.0 | 1.0 | 1.0 | 1.0 | 1.0 |
| Feed Composition | | | | | |
| MeOH/EC, molar ratio | 3.93 | 3.93 | 3.93 | 3.93 | 3.93 |
| Total Liquid Product Composition | | | | | |
| MeOH, wt % | 47.9 | 44.3 | 41.8 | 43.9 | 45.9 |
| EC, wt % | 15.8 | 15.3 | 13.7 | 15.1 | 14.2 |
| HEMC Intermediate, wt %[a] | 13.2 | 12.4 | 9.4 | 10.3 | 10.1 |
| DMC, wt % | 13.4 | 16.2 | 20.4 | 17.7 | 16.0 |
| EG, wt % | 9.7 | 11.8 | 14.7 | 12.2 | 10.0 |
| DMC/EG, Molar Ratio | 0.95 | 0.95 | 0.96 | 1.00 | 1.10 |
| EC Conv., % | 34.8 | 40.5 | 50.0 | 44.4 | 48.4 |

TABLE 2-continued

Transesterification of Ethylene Carbonate with Methanol Catalyzed by Cs-ZSM-5 with 25 wt % Cs (Condition: 100 psig)

| Temperature, ° F./° C. | 250/121 | 275/135 | 300/149 | 325/163 | 350/177 |
|---|---|---|---|---|---|
| DMC Select., % | 96.3 | 95.7 | 96.9 | 95.9 | 77.2 |
| EG Select., % | 101.0 | 101.0 | 101.1 | 95.8 | 69.9 |
| Byproduct Yield, wt %[b] | | | | | |
| $CO_2$, wt % | | 0.39 | | 2.89 | 4.14 |
| DME, wt % | | 0.00 | | 0.01 | 0.01 |
| $C_2$–$C_7$, wt % | | 0.00 | | 0.02 | 0.03 |
| Heavy Byproducts, wt %[c] | | 0.00 | | 2.56 | 10.85 |

[a]HEMC = 2-hydroxyethyl methyl carbonate
[b]Byproduct yield is calculated based on the total EC and methanol converted excluding conversion to HEMC.
[c]Heavy byproducts are mainly ethylene glycol oligomers.

Feed conversion is calculated based on EC converted during the transesterification reaction, since excessive amount of methanol (relative to EC) was used for all reactions. During EC/MeOH reaction, 2-hydroxyethyl methyl carbonate (HEMC) intermediate was also formed in addition to DMC and EG. The concentration of HEMC varies depending on the reaction conditions. Since it is recyclable along with unreacted EC, the intermediate carbonate is not considered as a byproduct. The feed conversion and product selectivity are defined as follows:

EC Conversion=(EC converted to products other than HEMC)/(total EC in feed)

DMC Selectivity=(moles of DMC formed)/(moles of EC converted to products other than HEMC)

EG Selectivity=(moles of EG formed)/(moles of EC converted to products other than HEMC).

The detailed operating conditions, feed ratio, material balance data, and results on EC conversion and dimethyl carbonate (DMC)/ethylene glycol (EG) selectivities for Cs-ZSM-5 containing 5.6 wt % cesium are summarized in Table 3.

TABLE 3

Transesterification of Ethylene Carbonate with Methanol Catalyzed by Cs-ZSM-5 with 5.6 wt % Cs (Condition: 100 psig)

| Temperature, ° F./° C. | 250/121 | 275/135 | 300/149 | 325/163 | 350/177 |
|---|---|---|---|---|---|
| WHSV, h$^{-1}$ | 1.9 | 1.9 | 1.9 | 1.9 | 1.9 |
| LHSV, h$^{-1}$ | 1.0 | 1.0 | 1.0 | 1.0 | 1.0 |
| Feed Composition | | | | | |
| MeOH/EC, molar ratio | 4.0 | 4.0 | 4.0 | 4.0 | 4.0 |
| Total Liquid Product Composition | | | | | |
| MeOH, wt % | 52.0 | 51.6 | 49.6 | 46.2 | 47.2 |
| EC, wt % | 25.0 | 24.0 | 22.1 | 18.5 | 20.0 |
| HEMC Intermediate, wt % | 12.5 | 10.9 | 8.9 | 5.5 | 3.6 |
| DMC, wt % | 5.8 | 7.7 | 11.3 | 18.0 | 16.8 |
| EG, wt % | 4.7 | 5.9 | 8.2 | 11.8 | 11.3 |
| DMC/EG, Molar Ratio | 0.85 | 0.90 | 0.95 | 1.05 | 1.03 |
| EC Conv., % | 16.4 | 21.0 | 29.1 | 44.7 | 44.9 |
| DMC Select., % | 84.7 | 88.4 | 93.9 | 96.8 | 89.0 |
| EG Select., % | 99.5 | 98.1 | 98.8 | 92.0 | 86.8 |

The detailed operating conditions, feed ratio, material balance data, and results on EC conversion and dimethyl carbonate (DMC)/ethylene glycol (EG) selectivities for K-Zeolite A (Molecular Sieves 3A) are summarized in Table 4.

TABLE 4

K-Zeolite A Catalyzed Transesterification of Ethylene Carbonate with Methanol (Condition: 100 psig)

| Temperature, °F./°C. | 250/121 | 275/135 | 300/149 | 325/163 | 350/177 |
|---|---|---|---|---|---|
| WHSV, h$^{-1}$ | 1.4 | 1.4 | 1.4 | 1.4 | 1.4 |
| LHSV, h$^{-1}$ | 1.0 | 1.0 | 1.0 | 1.0 | 1.0 |
| MeOH/EC Feed, molar ratio | 5.1 | 5.1 | 5.1 | 5.1 | 5.1 |
| Total Liquid Product Composition | | | | | |
| MeOH, wt % | 56.7 | 56.0 | 52.0 | 52.5 | 55.0 |
| EC, wt % | 18.9 | 18.1 | 10.5 | 11.6 | 11.5 |
| HEMC Intermediate, wt % | 8.7 | 7.3 | 7.6 | 5.3 | 4.4 |
| DMC, wt % | 8.9 | 10.6 | 17.3 | 17.9 | 15.4 |
| EG, wt % | 6.9 | 8.1 | 12.6 | 12.8 | 10.0 |
| DMC/EG, Molar Ratio | 0.89 | 0.90 | 0.95 | 0.96 | 1.06 |
| EC Conv., % | 27.9 | 32.9 | 52.8 | 54.3 | 58.9 |
| DMC Select., % | 89.1 | 90.1 | 94.3 | 95.1 | 71.5 |
| EG Select., % | 100.1 | 99.8 | 99.6 | 98.5 | 67.3 |

The comparison of activity and DMC/EG selectivity between the two Cs-ZSM-5 catalysts is illustrated in FIGS. 1–3. Both catalysts were evaluated under similar reaction conditions (100 psig, 1.0 h$^{-1}$ LHSV) and using 4:1 MeOH/EC mixture feed. FIGS. 1–2 clearly show that in a wide range of desirable reaction temperatures (250–325° F.) (120–163° C.), the ZSM-5 containing excessive amount of cesium (25 wt %) is more active (leading to higher EC conversion) and more selective in DMC (resulting in higher DMC yield) than the one containing cesium cations (5.6 wt %) mainly associated with zeolite framework polyanions. FIG. 2 also shows the stoichiometric catalyst decreases in DMC selectivity with decreasing temperature, while the DMC selectivity remains essentially constant with the catalyst containing excess cesium. Above 325 °F. (163 °C.), the reaction products begin to undergo thermal decomposition, which makes it difficult to compare catalyst performance. The EG selectivity is comparable for the two catalysts (FIG. 3).

The results of the K-Zeolite A catalyst show that, although the EG selectivity was quite constant (>99%) between 250–320° F. (120–163 °C.) under same conditions (100 psig pressure and 1.0 h$^{-1}$ LHSV), the DMC selectivity decreases with decreasing temperature. This is consistent with the results obtained using Cs-ZSM-5 with 5.6 wt % Cs as the catalyst. The DMC and EG selectivity vs. temperature is also plotted in FIG. 4. As demonstrated in FIG. 2, the DMC selectivity in the method of the invention remains essentially constant as temperature decreases to 250° F. (121 °C.).

EXAMPLE 4

This example demonstrates the effects of feed ratio on EC conversion and DMC/EG selectivity for EC/Methanol reaction catalyzed by Cs-ZSM-5 with 25 wt % Cs.

The experiments were performed according to the procedure described in Example 3 using Cs-ZSM-5 with 25 wt % Cs as the catalyst. Two mixture feeds, 5.4:1 and 3.9:1 MeOH/EC mixtures, were employed to study effects of feed ratio on EC conversion and DMC/EG selectivity under similar reaction conditions (100 psig, 1.0 h$^{-1}$ LHSV). The results summarized in Table 5 show that, while EC conversion is moderately higher with 5.4:1 MeOH/EC feed vs. 3.9:1 MeOH/EC feed at the same temperature due to the equilibrium of the reaction, the feed ratio has minimal effects on the DMC/EG selectivity. Therefore, the method of the invention can operate under a wider range of feed ratios without a significant effect on product selectivity.

TABLE 5

Effects of Feed Ratio on EC Conversion and DMC/EG Selectivity during EC/MeOH Reaction (Catalyst: Cs-ZSM-5 with 25 wt % Cs; Condition: 100 psig, 1.0 h$^{-1}$ LHSV)

| MeOH/EC Feed (Molar Ratio) | Temperature (°F./°C.) | EC Conversion % | DMC Selectivity % | EG Selectivity % |
|---|---|---|---|---|
| 5.4:1 | 250/121 | 41.0 | 96.0 | 100 |
| 5.4:1 | 275/135 | 52.8 | 95.2 | 100 |
| 5.4:1 | 300/149 | 62.4 | 96.1 | 100 |
| 3.9:1 | 250/120 | 34.8 | 96.3 | 100 |
| 3.9:1 | 275/135 | 40.5 | 95.7 | 100 |
| 3.9:1 | 300/149 | 50.0 | 96.9 | 100 |

Therefore, the examples demonstrate that the process of the invention, which uses a zeolite catalyst with an excess amount of cesium, has greater selectivity and conversion, while operating at a greater temperature range than prior art methods. The method of the invention is therefore more adaptable to commercial application.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A method for co-producing dialkyl carbonate and alkanediol comprising reacting alkylene carbonate with alkanol in the presence of a zeolite catalyst under process conditions, said catalyst comprising alkali metal, alkaline earth metal, or a combination thereof present in excess of a stoichiometric amount.

2. The method of claim 1 wherein said alkylene carbonate is ethylene carbonate.

3. The method of claim 1 wherein said alkanol is methanol.

4. The method of claim 1 wherein said alkali metal is cesium.

5. The method of claim 1 wherein said zeolite is selected from the group consisting of ZSM-5, zeolite beta, ZSM-22, ZSM-23, ZSM-48, ZSM-35, ZSM-11, ZSM-12, Mordenite, Faujasite, Erionite, zeolite USY, MCM-22, MCM-49, MCM-56, and SAPO.

6. The method of claim 5 wherein said zeolite is ZSM-5.

7. The method of claim 1 wherein said alkali metal, alkaline earth metal, or combination thereof present in excess of a stoichiometric amount is at least partially located within a zeolite pore.

8. The method of claim 7 wherein said alkali metal, alkaline earth metal, or combination thereof located within said zeolite pore is an oxide.

9. The method of claim 1 wherein said alkali metal, alkaline earth metal, or combination thereof is incorporated in said zeolite through impregnation.

10. The method of claim 1 wherein said process conditions comprise a reaction temperature of about 20° C. to about 300° C., a reaction pressure of about 14 to about 4000 psig, a liquid hour space velocity of about 0.1 to about 40 hr$^{-1}$, and a molar ratio of alkanol to alkylene carbonate of about 1–20.

* * * * *